United States Patent
Heismann

(10) Patent No.: US 7,138,635 B2
(45) Date of Patent: Nov. 21, 2006

(54) DETECTOR MODULE FOR CT AND/OR PET AND/OR SPECT TOMOGRAPHY

(75) Inventor: Bjoern Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 100 days.

(21) Appl. No.: 10/981,464

(22) Filed: Nov. 5, 2004

(65) Prior Publication Data

US 2005/0098735 A1    May 12, 2005

(30) Foreign Application Priority Data

Nov. 7, 2003    (DE)    ................................ 103 52 012

(51) Int. Cl.
| | |
|---|---|
| G01T 1/24 | (2006.01) |
| G01T 1/164 | (2006.01) |
| H01L 27/146 | (2006.01) |
| H01L 25/065 | (2006.01) |
| A61B 6/00 | (2006.01) |
| G01N 23/083 | (2006.01) |
| H05G 1/58 | (2006.01) |

(52) U.S. Cl. .......................... 250/370.09; 250/363.03; 250/370.06; 378/4; 378/116

(58) Field of Classification Search ........... 250/370.06, 250/370.12, 370.13, 371; 378/98.9, 116
See application file for complete search history.

(56) References Cited

U.S. PATENT DOCUMENTS

| | | | |
|---|---|---|---|
| 4,651,005 A * | 3/1987 | Baba et al. ..................... 378/5 |
| 6,399,951 B1 * | 6/2002 | Paulus et al. .......... 250/370.13 |
| 6,449,331 B1 | 9/2002 | Nutt et al. |
| 6,490,476 B1 | 12/2002 | Townsend et al. |
| 6,920,196 B1 * | 7/2005 | Ueno et al. ..................... 378/19 |
| 6,965,661 B1 * | 11/2005 | Kojima et al. .................. 378/4 |
| 2003/0004405 A1 | 1/2003 | Townsend et al. |
| 2005/0105687 A1 * | 5/2005 | Heismann et al. ......... 378/98.8 |

FOREIGN PATENT DOCUMENTS

| | | |
|---|---|---|
| DE | 102 12 638 A1 | 10/2003 |
| EP | 0 932 842 B1 | 4/2002 |

OTHER PUBLICATIONS

T. Beyer et al, "PET/CT-Tomographie mit neuem PET-Detektormaterial für ultraschnelle Bildgebung in der klinischen Onkologie", Electromedia 70 (2002), pp. 167-172.
Heinz Morneburg, "Bildgebende Systeme für die medizinische Diagnostik", 3. Auflage, 1995, pp. 470-501.

* cited by examiner

*Primary Examiner*—David Porta
*Assistant Examiner*—Frederick F. Rosenberger
(74) *Attorney, Agent, or Firm*—Harness, Dickey & Pierce, P.L.C.

(57) ABSTRACT

A detector module is for CT and/or PET and/or SPECT examinations, and includes a number of measuring channels. Each measuring channel includes a direct converter for directly converting incident measuring radiation into analog electric signals, a pulse generator connected to the direct converter, for generating counting pulses as a function of the received electric signals, and a counting device that counts the received counting pulses over a prescribable time period and outputs the result. Arranged between the counting device and the pulse generator is an externally drivable changeover unit that can be used to switch over between the counting device and an event detector that registers and outputs for each received counting pulse the time and the associated measuring channel or an item of location information assigned to this measuring channel. The present detector module is of simple design.

18 Claims, 2 Drawing Sheets

DETECTOR MODULE FOR CT AND/OR PET AND/OR SPECT TOMOGRAPHY

The present application hereby claims priority under 35 U.S.C. §119 on German patent application number DE 10352012.0 filed Nov. 7, 2003, the entire contents of which are hereby incorporated herein by reference.

FIELD OF THE INVENTION

The present invention generally relates to a detector module for CT and/or PET and/or SPECT examinations having a number of measuring channels. Preferably it relates to one wherein each measuring channel includes a direct converter for directly converting incident measuring radiation into analog electric signals, a pulse generator, connected to the direct converter, for generating counting pulses as a function of the received electric signals, and a counting device that counts the received counting pulses over a prescribable time period and outputs the result.

BACKGROUND OF THE INVENTION

Examinations are carried out with the aid of computed tomographs in many problem areas in medicine. In this case, the computed tomograph includes an X-ray source and a detector module, opposite the X-ray source, with a number of measuring channels that are formed by individual detector elements. For the purpose of spatially resolved detection of the X-radiation, the detector elements are generally arranged next to one another in one or more rows. Findings relating to the distribution of material within the object to be examined can be obtained from the spatially resolved measurement of the attenuation of the X-radiation by the object to be examined located between the X-ray source and detector module.

Known on the one hand, for detecting X-radiation are detectors having indirect converters that are assembled from a scintillator material with a downstream photodetector. The scintillator converts the incident X-radiation into optical radiation that is subsequently detected by the photodetector. The number of photons produced per X-ray quantum is generally approximately proportional to its quantum energy in this case. This technique uses integration over the electric signal received by the photodetector over a prescribed time interval. The intensity of the received X-radiation is then yielded by dividing the value integrated by the detector by the mean quantum energy, to be determined stochastically, per X-ray quantum.

Also known for detecting X-radiation are specific semiconductor materials in which the incident X-radiation generates charge carriers directly. The number of the charge carriers generated in these direct converters per X-ray quantum is generally approximately proportional to its quantum energy in this case.

A counting method is also known for computed tomographs instead of integration over the analog electric signal received by the converter. Thus, DE 102 12 638 A1 exhibits a detector module for a computed tomograph that has a number of detectors or measuring channels which detect the X-radiation on the basis of direct converters. Each converter is connected to a pulse generator for generating counting pulses as a function of the received electric signals. The pulse generator relays the pulses to a counting device that counts the received counting pulses over a prescribable time period and outputs the result.

In this configuration, the electronics of the detectors have substantially fewer analog parts than the electronics of conventional detectors. The electronics provided can therefore be smaller, more cost-effective and more noise-immune. The detector module represented in this printed publication further includes a threshold logic unit composed of a number of parallel-connected comparators as part of the pulse generator, each of the comparators being assigned a counter in the counting device in order to be able to count X-ray quanta of different energy independently of one another. The detection of the incident X-radiation is enabled in this way with regard both to intensity and to the quantum energy of the individual X-ray quanta.

In addition to computed tomography (CT), positron emission tomography (PET) has also become increasingly widespread in medical diagnostics of recent years. Whereas computed tomography is concerned with an anatomical imaging technique, PET permits, for example, the visualization and quantification of metabolic activities in vivo.

Positron emission tomography utilizes the particular properties of positron radiators and positron annihilation for the purpose of quantitative determination of the functioning of organs or cell zones. The patient is administered appropriate positron radiators in this case before the examination. During decay of a positron radiator, a proton is converted into a positron, a neutron and a neutrino. However, the positron is not directly detected, since its range is limited to a few mm. In the patient's tissue, the positron is braked by scattering processes at the shells of neighboring atoms and is captured by a shell electron.

Annihilation produces two gamma quanta that fly apart in opposite directions. The energy of the two gamma quanta is 511 keV in each case on the basis of the law of conservation of energy and impulse. If the gamma quanta of two opposite detector elements is measured within a specific time, the location of the annihilation is established at a position on the connecting line between these two detector elements. This is utilized for generating images in PET.

A combined measurement using both CT and PET techniques is desired in many instances on the basis of the different information the two techniques return. Thus, for example, the article by T. Beyer et al., entitled PET/CT-Tomographie mit neuem PET-Detektormaterial für ultraschnelle Bildgebung in der klinischen Onkologie [PET/CT tomography with the aid of new PET detector material for ultrafast imaging in clinical oncology], electromedia 70 (2002), pages 167–172 discloses a combined PET/CT tomograph which can be used to produce complementary PET and CT images in a short time in a single examination. The detector modules for computed tomography and for positron emission tomography are mounted in the same installation in this case such that images produced with the aid of the two techniques can be registered exactly and without any problem. US 2003/0004405 A1 also discloses a combined PET and X-ray CT tomograph that can be used to take CT and PET pictures of an object to be examined directly one after another. The two detector modules, the detector module for CT and the detector module for PET, are mounted in this case on a common support inside the gantry.

The two abovementioned printed publications indicate that so far CT detectors and PET detectors have been implemented using different technologies. The detector modules for CT systems are generally based on integrating detectors, for example having GdOS or CdWO scintillators. By contrast, PET systems operate with counting scintillator detectors based on BGO and LSO.

At first glance, the measuring requirements differ greatly between the systems. Computed tomography must process very large quantum currents, the time resolution being in the region of from 200 μs to 600 μs in this case. By contrast, PET makes use of a coincidence measurement. This requires a high time resolution which is, for example, approximately 300 ns given the use of BGO and approximately 30–50 ns given the use of LSO, while the quantum fluxes are smaller by orders of magnitude than in the case of computed tomography. Instead of an X-ray tube, a positron emission tomograph makes use in the body of the patient of the decaying radionuclides at functional key groups, for example at tumor cells, as radiation source.

As already explained, upon decay of the nuclides, two gamma quanta are emitted in opposite directions. In the case of PET the detector module must generally cover the greater part of the gantry arc length for the purpose of detection. It is subdivided into detector elements having a side length of a few mm. Each detector element, also designated as a measuring channel in the present patent application, generates upon detection of a gamma quantum an event record that specifies the time and the detection location, that is to say the corresponding detector element.

These information items are transmitted to a fast logic unit and compared. If two events coincidence within a maximum time period, it is assumed that there is a gamma decay process on the connecting line between the two associated detector elements. As in the case of CT, the PET image is then reconstructed using a tomography algorithm, that is to say the so called back projection.

U.S. Pat. No. 6,449,331 B1 describes a combined PET and CT detector module that is mounted on a support inside the gantry of a combined PET and CT installation. The individual detector elements of the detector module respectively include a scintillator crystal with a downstream photodetector. LSO is used as scintillator material, in the way known from positron emission tomographs.

The photodetector is connected, on the one hand, to an event detector that registers all the reception events, and, on the other hand, to an integration unit that integrates over the received signal. The detector module operates in three operating modes.

In a first operating mode as PET detector, it outputs an item of information relating to the time and the location of a reception event via the event detector. In a second operating mode, the detector module operates as a standard CT detector in the case of which the signal received by the photodetector is integrated with the aid of the integration unit. In a third operating mode, individual events are counted in the CT operation in order to obtain a CT image therefrom.

In the course of the dead times of the indirect converter (scintillator crystal and photodetector), this third operating mode can be used only given very small quantum fluxes of the X-radiation, and so it is generally necessary to switch over to this second operating mode in the integration unit given the quantum fluxes customary for CT. The implementation of such a detector module remains, however, complicated since, in addition to the event detector there is also a need for the integration unit for CT measurements.

SUMMARY OF THE INVENTION

An object of an embodiment of the present invention resides in specifying a detector module that is of simple design and equally suitable for CT and PET measurements.

An object may be achieved with the aid of the detector module. Advantageous refinements of the detector module can be gathered from the following description and the exemplary embodiment.

In a known way, the present detector module for CT and/or PET and/or SPECT examinations has a number of measuring channels in the form of detector elements of which each measuring channel includes a direct converter for directly converting incident measuring radiation into analog electric signals, a pulse generator, connected to the direct converter, for generating counting pulses as a function of the received electric signals, and a counting device that counts the received counting pulses over a prescribable time period and outputs the result. In addition, arranged between the counting device and the pulse generator is an externally drivable changeover unit that can be used to switch over between the counting device and an event detector also provided that registers and outputs for each received counting pulse the time and the associated measuring channel or an item of location information assigned to this measuring channel.

The direct converter is preferably designed here as a semiconductor converter. The present detector module can be switched over, using the changeover unit that can be driven or configured by an operator, between an operating mode in which the counting pulses are added up in order to obtain CT measured data, and an operating mode in which the location and the time of individual events are registered and output in order to obtain PET data. This provides a detector module that can be used both for CT and for PET measurements. In particular, this detector module can therefore be used in a combined CT/PET installation. Of course, however, the detector module is also suitable for SPECT (Single Photon Emission Computed Tomography).

By contrast with a part of the prior art mentioned at the beginning, the present detector module of one embodiment therefore offers the advantage that now only one detector module need be used for combined CT/PET measurements. By contrast with the detector module of U.S. Pat. No. 6,449,331 B1, it offers the advantage of a simpler design, since it is possible to dispense with an additional integration unit for CT measurements.

The present detector module of one embodiment is based on the use of counting detectors on the basis of direct converters, in particular of counting semiconductor detectors, for CT detection. Such a detector module is equipped, by way of an embodiment of the present invention, with an additional mode in which a counting event in the electronics of a measuring channel that corresponds to a pixel of the CT image does not lead to incrementation of a counter, an item of event information including specification of time and location being generated instead. This mode can be communicated to the detector module via a configuration value that can, for example, be input via a graphics user interface of the installation in which the detector module is used.

In the case of the present detector module, the pulse generator preferably includes a threshold logic unit on the basis of which a counting pulse is generated as soon and as often as the received electric signal exceeds the set threshold value. In a preferred development, this threshold logic unit includes a number of parallel-connected comparators of which each comparator has a different threshold value, and each comparator is assigned a separate counter in the counting device. The respectively assigned counter is incremented by one unit in this way only whenever the quantum energy of a radiation quantum of the received measuring radiation exceeds the threshold value of the respective comparator. Owing to this refinement, an item of information relating to the distribution of the quantum energy of the individual X-ray quanta can also be obtained in the operating mode of the CT measurement in addition to the intensity. This refinement therefore corresponds to a development of the detector module disclosed in DE 102 12 638 A1, the disclosure content of which is explicitly incorporated by reference into the present patent application.

Since the ideal thicknesses of the direct converters for CT and PET differ very strongly from the point of view of cost/benefit efficiency on the basis of the different quantum energies of 30–14 keV and 511 keV, respectively, it is necessary to include when dimensioning the present detector module. The dimensions of the direct converter that are suitable for CT measurements and which in the case of CdZnTe, for example, must only have a thickness of a few mm, are preferably used in this case in order, for example, to achieve a degree of absorption of >95% for the X-radiation. It is taken into account in this case that the quantum efficiency requirements for PET are by far not so high as in the case of CT, and so adequate measurement results can still be obtained for PET even by using such thin direct converters. Of course, it is also possible to use appropriately thicker direct transducers in order to obtain a higher quantum efficiency for the PET.

BRIEF DESCRIPTION OF THE DRAWINGS

The present detector module is explained again, in more detail, below with the aid of an exemplary embodiment in conjunction with the drawings, in which.

DETAILED DESCRIPTION OF THE EXEMPLARY EMBODIMENTS

Figure 1:
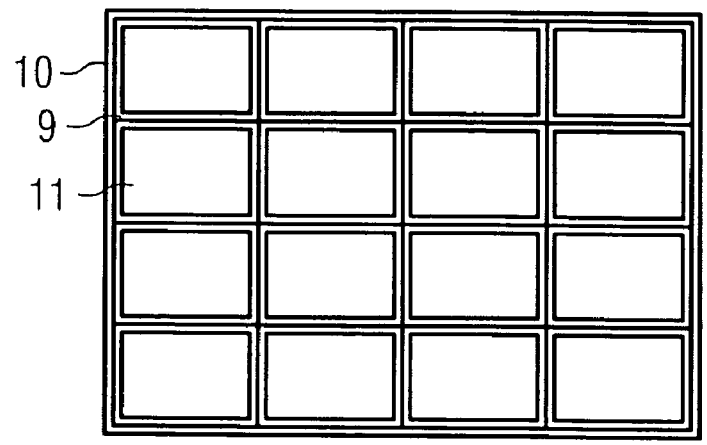
FIG. 1 shows a plan view of a detector module in accordance with an embodiment of the present invention that consists of a multiplicity of detector elements.

FIG. 1 shows an example of the detector module 10 of an embodiment of the present invention including a multiplicity of detector elements 9. In this example, the individual detector elements 9, by which the measuring channels of the detector module 10 are formed, are to be seen in plan view. In this example, the number of detector elements 9 is limited for reasons of clarity and as a rule is a multiple of the number to be seen in the figure.

The detector elements 9 are arranged in a known way next to one another in an array. On the side facing the measuring radiation, each detector element 9 has a receiving face 11 for the measuring radiation, which is formed in the present example by the material of the direct converter, a semiconductor material. Consideration is given here to CdZnTe (cadmium-zinc-tellurite), CdTe (cadmium tellurite) or $HgI_2$ (mercury iodide) in particular, as semiconductor materials. As a consequence of a received X-ray quantum, these materials are capable of generating an electric signal directly, that is to say without a detour via optical radiation. The level of the signal is approximately proportional here to the quantum energy of the received radiation quantum.

Figure 2:
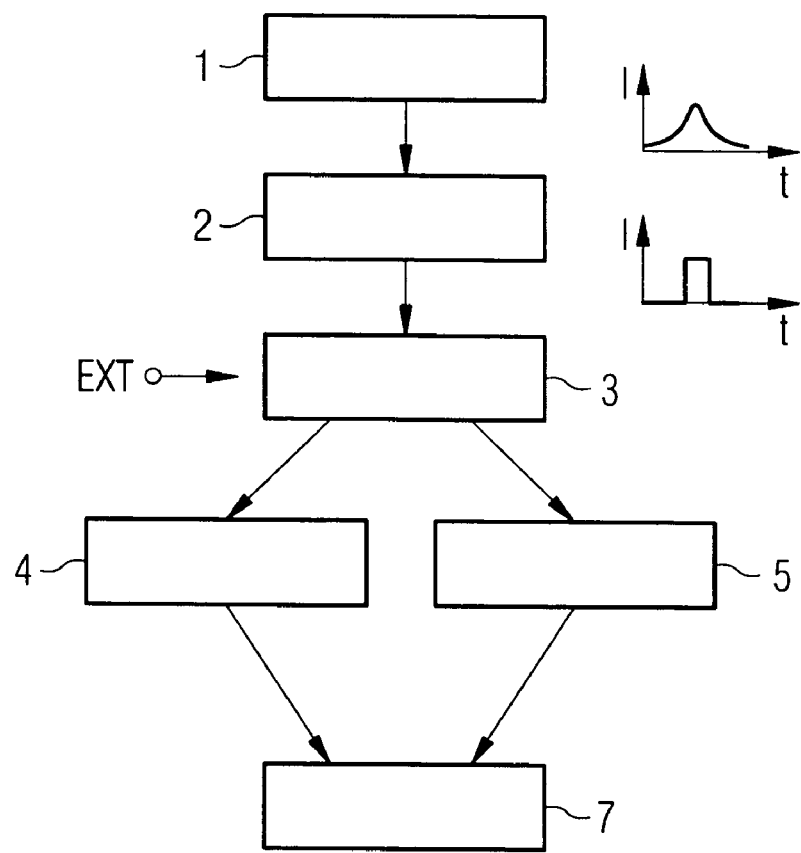
FIG. 2 shows a diagram of essential elements of the present detector module in accordance with an exemplary embodiment.

Finally, FIG. 2 shows a diagram of the elements of a detector module in accordance with an exemplary embodiment of the present invention, reference being made in this case to the individual measuring channel of the detector module.

Each detector element of the detector module includes the X-ray converter, which is designed as a direct converter 1 and converts incident radiation quanta into current pulses that are output as an electric signal, as is to be seen in the right-hand part of the figure. The electric signal is received by a pulse generator 2 that includes a threshold logic unit in the present example and generates a counting pulse as a function of the received electric signal, that is to say upon receiving a signal that originates from a radiation quantum, as is likewise to be seen in the right-hand part of the figure.

As a rule, a signal amplifier is additionally provided between the direct converter 1 and the pulse generator 2. The counting pulses pass via a changeover unit 3 either to a counting device 4 or to an event detector 5. The changeover unit 3 can be switched over by way of an external input between two switching states which correspond to the two operating modes of the detector module. The counting pulses of the pulse generator 2 pass to the counting device 4 in the first mode, and to the event detector 5 in the second mode.

In the CT operation of the module, the counting pulses are counted with the aid of the counter or counters provided in the counting device 4 over a prescribable time period, the measuring interval, that is to say the counter is incremented by one unit with each counting pulse. Upon expiry of the time period, the correspondingly obtained value is output via an interface 7. If the configuration of the detector module with a number of comparators and a number of counters per measuring channel is used, as is explained in conjunction with the following figure, the output result is a combination of a number of count values, for example 5-3-2-8-5-1, each value originating from one of the counters and being capable of being assigned to a specific energy band of the counted quanta.

During operation of this detector module for PET measurements, the counting pulses, which generate for each counting pulse an item of information relating to the time and the location of the occurrence, are passed from the pulse generator 2 to the event counter 5. In this process, the time can be a system time or a time interval relative to a reference instant. The location information can comprise either the information relating to the measuring channel from which the counting pulse was obtained, or, in a fashion derived therefrom, the information relating to the location inside the detector module at which the gamma quantum was detected. Thus, the event detector 5 supplies, for example with each received counting pulse, the number of the associated measuring channel and a corresponding item of time information (for example #13748/183 ns). These data are also output via the common interface 7.

Figure 3:
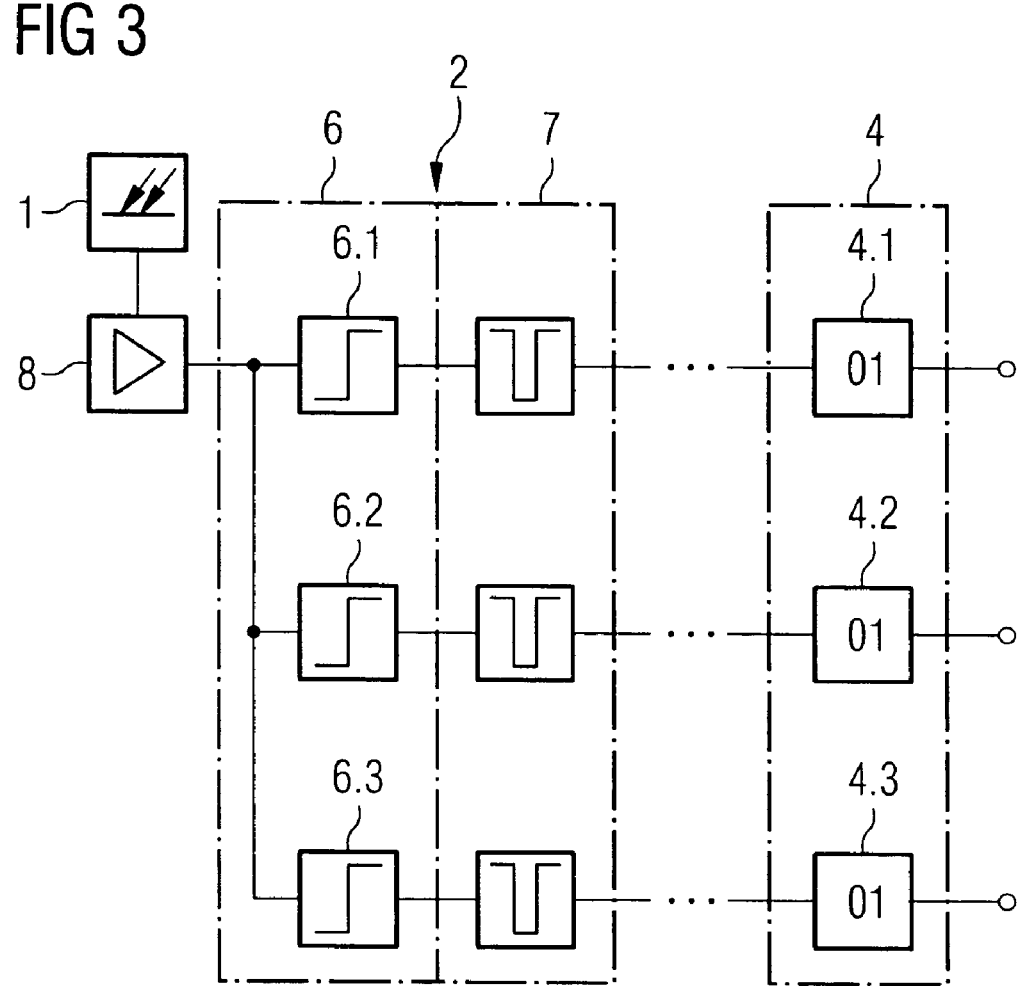
FIG. 3 shows a diagram of individual elements of the pulse generator and of the counting device in accordance with a preferred embodiment of the present detector module.

Finally, FIG. 3 shows components of the pulse generator 2 and of the counting device 4 as they have been explained in conjunction with FIG. 2, in accordance with an advantageous configuration of an embodiment of the present detector module. In this configuration, the pulse generator 2 includes a threshold logic unit 6 having three parallel-connected comparators 6.1, 6.2 and 6.3. The signal obtained from the direct converter 1 is fed in this case to the pulse generator 2 via an amplifier 8.

Each of the parallel-connected comparators 6.1, 6.2 and 6.3 is allocated another freely settable threshold value. For example, the comparator 6.1 can be allocated the least significant threshold value, and the comparator 6.3 the most significant. The comparators are designed in order to compare the electric signal obtained from the amplifier 8 with their respective threshold value and to output a positive signal when the signal received from the amplifier 8 is higher than the respective threshold value. Connected in each case to the comparators is a pulse logic unit 7 that generates a counting pulse upon obtaining a positive signal from the respective comparator.

In the present example, each comparator 6.1, 6.2 and 6.3 in the counting device 4 is assigned a dedicated counter 4.1, 4.2 and 4.3. If the corresponding detector element receives an X-ray quantum whose quantum energy is above the threshold value of the comparator 6.2 and thus above the threshold value of the comparator 6.1 but below the threshold value of the comparator 6.3, then both the comparator 6.1 and the comparator 6.2 output a positive output signal. In consequence, the counters 4.1 and 4.2 are incremented by the value 1. By contrast, the counter 4.3 remains unchanged.

Therefore, the number of the received X-ray quanta whose quantum energy corresponds to a respective threshold range can easily be calculated by way of the difference between the counter readings of the individual counters of comparators of neighboring threshold values. The X-ray quanta in four quantum energy ranges can therefore be distinguished for the refinement illustrated by way of example in FIG. 3.

Thus, it is possible with the aid of such a refinement to carry out not only, as it were, CT and PET or SPECT recordings using only one detector module. Rather, spectral information relating to the detected X-ray quanta is also rendered possible in the case of CT measurements.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector module, comprising:
   a plurality of measuring channels, each measuring channel including
   a direct converter, adapted to directly convert incident measuring radiation into analog electric signals,
   a pulse generator, connected to the direct converter, adapted to generate counting pulses as a function of analog electric signals,
   a counting device, adapted to count the counting pulses over a prescribable time period and output a result, and
   an externally drivable changeover unit, arranged between the counting device and the pulse generator, adapted to switch over between the counting device and an event detector that registers and outputs, for each counting pulse, at least one of a time and an associated measuring channel, and an item of location information assigned to the associated measuring channel.

2. The detector module as claimed in claim 1, wherein the direct converter includes a semiconductor detector.

3. The detector module as claimed in claim 2, wherein the semiconductor detector is formed from at least one of $HgI_2$, CdZnTe, CdTe and TlBr.

4. The detector module of claim 3, wherein the detector module is for at least one of computed tomography (CT), positron emission tomography (PET) and Single Photon Emission Computed Tomography (SPECT).

5. The detector module as claimed in claim 3, wherein the pulse generator includes a threshold logic unit.

6. The detector module as claimed in claim 5, wherein the threshold logic unit is formed from a number of parallel-connected comparators, each with a threshold, each comparator being assigned a counter of the counting device, in order to increment the respectively assigned counter by one unit only whenever quantum energy of a radiation quantum of measured radiation exceeds the threshold of the respective comparator.

7. The detector module of claim 2, wherein the detector module is for at least one of computed tomography (CT), positron emission tomography (PET) and Single Photon Emission Computed Tomography (SPECT).

8. The detector module as claimed in claim 2, wherein the pulse generator includes a threshold logic unit.

9. The detector module as claimed in claim 8, wherein the threshold logic unit is formed from a number of parallel-connected comparators, each with a threshold, each comparator being assigned a counter of the counting device, in order to increment the respectively assigned counter by one unit only whenever quantum energy of a radiation quantum of measured radiation exceeds the threshold of the respective comparator.

10. The detector module as claimed in claim 1, wherein the pulse generator includes a threshold logic unit.

11. The detector module as claimed in claim 10, wherein the threshold logic unit is formed from a number of parallel-connected comparators, each with a threshold, each comparator being assigned a counter of the counting device, in order to increment the respectively assigned counter by one unit only whenever quantum energy of a radiation quantum of measured radiation exceeds the threshold of the respective comparator.

12. The detector module of claim 1, wherein the detector module is for at least one of computed tomography (CT), positron emission tomography (PET) and Single Photon Emission Computed Tomography (SPECT).

13. A detector module, comprising:
    a plurality of measuring channels, each measuring channel including
    means for directly converting incident measuring radiation into analog electric signals,
    means for generating counting pulses as a function of the analog electric signals,
    means for counting the generated counting pulses over a prescribable time period and outputting a result, and
    means, arranged between the means for counting and the means for generating, for switching over between the means for counting and an event detector that registers and outputs, for each generated counting pulse, at least one of a time and an associated measuring channel, and an item of location information assigned to the associated measuring channel.

14. The detector module as claimed in claim 13, wherein the means for directly converting includes a semiconductor detector.

15. The detector module as claimed in claim 14, wherein the semiconductor detector is formed from at least one of $HgI_2$, CdZnTe, CdTe and TlBr.

16. The detector module as claimed in claim 13, wherein the means for generating includes a threshold logic unit.

17. The detector module as claimed in claim 16, wherein the threshold logic unit is formed from a number of parallel-connected comparators, each with a threshold, each comparator being assigned a counter of the means for counting, in order to increment the respectively assigned counter by one unit only whenever quantum energy of a radiation quantum of the received measured radiation exceeds the threshold of the respective comparator.

18. The detector module of claim 13, wherein the detector module is for at least one of computed tomography (CT), positron emission tomography (PET) and Single Photon Emission Computed Tomography (SPECT).

* * * * *